US012558245B2

(12) United States Patent
Mazzarolo et al.

(10) Patent No.: US 12,558,245 B2
(45) Date of Patent: Feb. 24, 2026

(54) POLYCENTRIC HINGE FOR A KNEE BRACE AND KNEE BRACE COMPRISING SUCH A POLYCENTRIC HINGE

(71) Applicant: ALPINESTARS RESEARCH S.P.A., Maser (IT)

(72) Inventors: Giovanni Mazzarolo, Coste di Maser (IT); Stefano Borsato, Biadene di Montebelluna (IT); Paolo Piovesan, Maser (IT); Roberto Gorza, Pedavena (IT)

(73) Assignee: ALPINESTARS RESEARCH S.P.A., Maser (IT)

( * ) Notice: Subject to any disclaimer, the term of this patent is extended or adjusted under 35 U.S.C. 154(b) by 259 days.

(21) Appl. No.: 18/681,977

(22) PCT Filed: Aug. 5, 2022

(86) PCT No.: PCT/IB2022/057297
§ 371 (c)(1),
(2) Date: Feb. 7, 2024

(87) PCT Pub. No.: WO2023/017380
PCT Pub. Date: Feb. 16, 2023

(65) Prior Publication Data
US 2025/0120835 A1      Apr. 17, 2025

(30) Foreign Application Priority Data
Aug. 9, 2021      (IT) ........................ 102021000021527

(51) Int. Cl.
A61F 5/01 (2006.01)

(52) U.S. Cl.
CPC .... A61F 5/0123 (2013.01); *A61F 2005/0139* (2013.01)

(58) Field of Classification Search
CPC ........ A61F 5/0123; A61F 5/0125; A61F 5/01; A61F 5/0102; A61F 5/013; A61F 5/055;
(Continued)

(56) References Cited

U.S. PATENT DOCUMENTS 4,523,585 A      6/1985  Lamb et al.
4,632,096 A  *  12/1986  Harris ................... A61F 5/0102
602/16

(Continued)

FOREIGN PATENT DOCUMENTS

EP             482809 A1      4/1992
WO        2013181366 A1      12/2013

OTHER PUBLICATIONS

International Search Report and Written Opinion of the International Application No. PCT/IB2022/057297, mailed Nov. 16, 2022, 10 pg.

*Primary Examiner* — Daniel A Miller
(74) *Attorney, Agent, or Firm* — Fredrikson & Byron, P.A.

(57) ABSTRACT

A polycentric hinge for a knee brace, and knee brace including such hinge. The hinge includes first couple of hinge arms, second couple of hinge arms, and hinge body for hinging together the first couple of hinge arms and second couple of hinge arms. Each hinge arm of the first couple and each hinge arm of the second couple has a first end pivotally enclosed inside said hinge body and a second end pivotally fixed to a mounting frame.
The hinge body is provided with pivoting means adapted to engage said first ends to define four different and spaced apart rotation axes extending transversally with respect to a longitudinal axis of the hinge body. The first ends of each hinge arm of the second couple can be connected to each
(Continued)

other, so that rotation of the mounting frame causes rotation of both hinge arms around their respective rotation axes.

21 Claims, 8 Drawing Sheets

(58) Field of Classification Search
CPC ...... A61F 2005/0139; A61F 2005/0144; A61F 2005/0179; A61F 2005/0167; A61F 2005/0158; A61F 2005/0165; A61F 2005/0174; A61F 2005/0188; A61F 2005/0146; A61F 2005/0137; A61F 2005/016; A61F 2005/0148; A61F 2/642; A61F 2/644; A61F 2/74; A61F 2/68; A61F 2/604; A61F 2/744; A61F 2/748; A61F 2002/5073; A61F 2002/6614; A61F 2002/6607; A61F 2002/6818
USPC .......................................................... 602/16
See application file for complete search history.

(56) References Cited

U.S. PATENT DOCUMENTS

| | | | |
|---|---|---|---|
| 4,886,054 A | 12/1989 | Castillo et al. | |
| 4,961,416 A | 10/1990 | Moore et al. | |

* cited by examiner

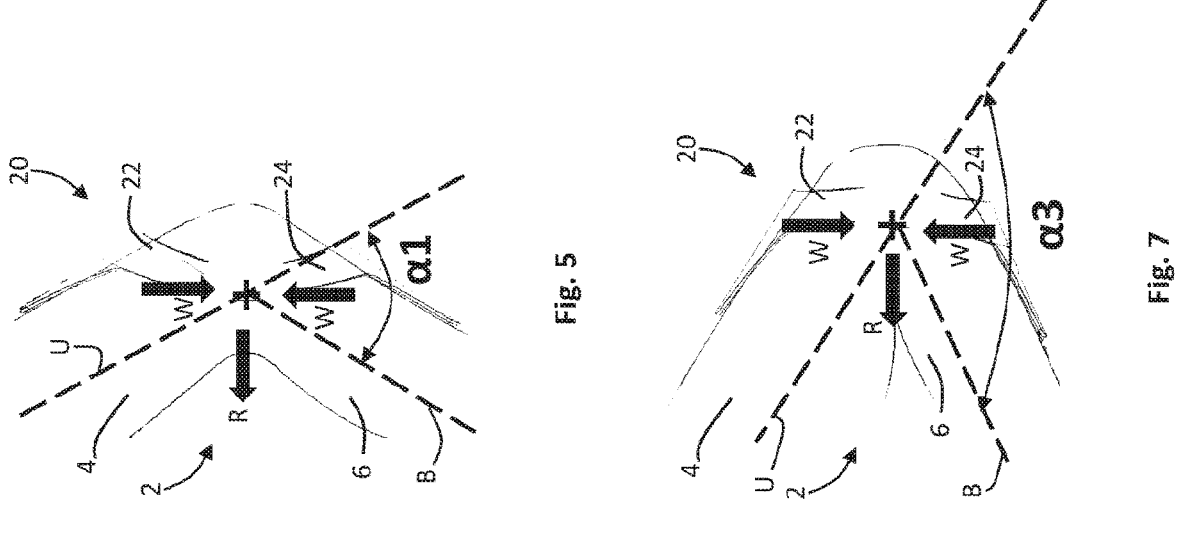
Fig. 5
Fig. 7
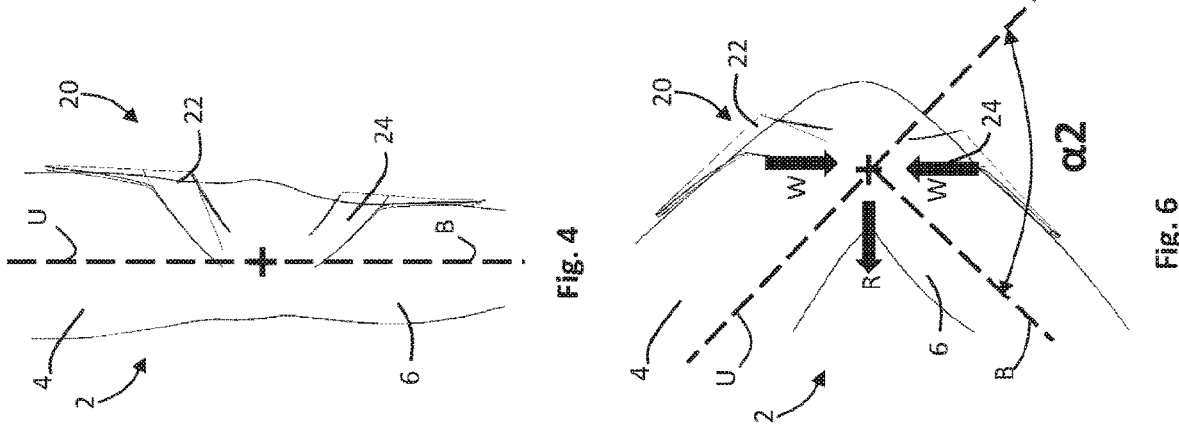
Fig. 4
Fig. 6

POLYCENTRIC HINGE FOR A KNEE BRACE AND KNEE BRACE COMPRISING SUCH A POLYCENTRIC HINGE

RELATED APPLICATIONS

This application is a 35 U.S.C. 371 national stage filing from International Application No. PCT/IB2022/057297, filed Aug. 5, 2022, which claims priority to Italian Patent Application No. 102021000021527, filed Aug. 9, 2021. The entire contents of each of these applications is incorporated herein by reference in their entirety.

The present invention relates to a polycentric hinge for use with a knee brace. Moreover, the present invention relates to a knee brace comprising such a polycentric hinge.

FIELD OF THE INVENTION

Nowadays the use of knee brace protectors is largely diffused during sport activities, like for example motorcycling, cycling, skiing, etc.

BACKGROUND

The knee braces have been studied to protect users from injuries coming from impacts and unnatural movements of the knee. In particular, in motocross activities a high risk exists that the knee of the rider hits an obstacle or undergoes unnatural flexion, torsion or extension movements.

Generally, the knee brace comprises an upper frame member, designed to be fastened to the upper part of the user's leg, and a lower frame member, designed to be fastened to the lower part of the user's leg.

The upper and lower frame members are connected to each other by means of a single or double hinge which enables the frames to follow the flexion movement of the leg, preventing at the same time knee injuries coming from hyper-rotation, hyper-flexion or hyper-extension of the knee joint.

In motorcycling application, in view of the high forces involved, the frames are also made of rigid material, so as to offer an improved protection to the knee against direct impacts.

Moreover, to provide enhanced protection to the knee against impacts, knee braces are usually provided with a semi-rigid or rigid protecting cup, designed to be superimposed in use over the user's patella.

Such a protecting cup is connected to the rigid frames by means of a slidable mechanism which has the function to maintain the protecting cup in the correct position during the knee brace's movements. The slidable mechanism is usually coupled to the articulation hinge of the knee brace.

Even if the above mentioned knee braces are greatly appreciated, they have some drawbacks.

The first issue is related to the actual movements followed by the knee joint when the leg is flexing.

As a matter of fact, the relative movement of the upper and lower parts of the leg is not a pure rotation, but a combination of different linear and rotational movements which result in a roto-translational movement.

Even if the use of polycentric hinges is known, namely hinges having more than two centers of rotation, the known hinges are still not able to adapt to the roto-translational movements of the knee joint.

As schematically shown in FIGS. 1A-1B, which are enclosed to the present description to better illustrate the technical problem faced and solved by the present invention, when the frames are fastened to the user's leg and the leg is flexed, the movement of the leg would cause a reduction of the distance between the facing ends of the upper frame A and lower frame B.

However, these ends are connected to the articulation hinge and thus are mutually blocked, consequently a reduction of the distance between these facing ends (schematically shown in FIG. 1B by the arrows P) results in an outward movement of the articulation hinge and therefore in an outward movement of the protecting cup C. Such a movement is schematically shown in FIG. 1B by the arrow T.

Moreover, with reference to FIG. 1A, the gap between the patella of the user and the protecting cap C is indicated by the letter J1, while the gap between the upper frame A and the protecting cup C and the gap between the lower frame B and the protecting cup C are respectively indicated by the letter Y1 and K1.

As schematically shown in FIG. 1B, the outward movement of the articulation hinge results in a bigger gap being formed between the protecting cup C and the knee brace frames A, B (these gaps being indicated by the letters Y2 and K2) and in a bigger gap being formed between the protecting cup C and the patella of the user (this gap being indicated by the letter J2). The bigger these gaps Y2, K2, J2 are, the lower will be the protection offered by the knee brace to the knee of the user against frontal and side impacts.

Furthermore, the outward movement of the articulation hinge pulls the latter away from the right position which would be at the lateral sides of the knee.

As a consequence of such a movement, the knee joint is no longer laterally protected and thus the knee is exposed to unnatural movements in case of a side impact.

At the same time, even if no impact occurs, the rider during the use of the knee brace can have a bad feeling since the knee joint is not properly wrapped by the knee brace. Moreover, the outward movement of the articulation hinge also affects the freedom of movement of the knee joint which is forced to follow a movement which does not match the natural movement of the knee during the flexion. This reduces the comfort of the user who might also encounter problems in having a full control of the motorcycle.

Finally, the knee braces are generally worn under the pants. Consequently, the outward movement of the protecting cup with respect to the frames, when the knee brace is flexed, generates an uncomfortable pressure on the leg due to the overlying pants. As a matter of fact, the pants used by the riders for aerodynamics and safety reasons need to stay closer to the user's leg and thus they are not able to compensate for such a movement.

BRIEF SUMMARIES OF OBJECTS OF THE INVENTION

The object of the present invention is to provide a polycentric hinge for a knee brace which solves at least partly the above mentioned problems and drawbacks.

In particular, an aim of the present invention is to provide a polycentric hinge for a knee brace suitable to better adapt itself to the natural movements of the knee.

Moreover, an aim of the present invention is to provide a polycentric hinge for a knee brace suitable for facilitating the mutual movement between the upper and the lower frames of the knee brace.

Furthermore, an aim of the present invention is to provide a polycentric hinge suitable for offering an improved protection to the knee joint of the user, without hindering the freedom of movement thereof.

A further aim of the present invention is to provide a polycentric hinge suitable for offering an improved comfort to the user, assuring a high stability to the knee joint.

Finally, an aim of the present invention is to provide a knee brace able to offer an improved protection against impacts and unnatural movements of the knee joint, without affecting the freedom of movement of the user.

These and other objects and aims are achieved by the polycentric hinge according to claim 1 and by the knee brace according to claim 21.

BRIEF DESCRIPTIONS OF THE DRAWINGS

The advantages and the characteristic features of the invention will appear more clearly from the following description of preferred, but not exclusive, embodiments of the polycentric hinge and the knee brace with reference to the accompanying figures in which:

FIGS. 1A and 1B schematically shown a prior art knee brace in two different operative conditions;

FIG. 3A shows an inner view of a component of the polycentric hinge of FIG. 3;

FIGS. 3B, 3C and 3D are respectively a side view, an outer view and a perspective inner view of the component of FIG. 3A;

FIG. 3E shows an inner view of a further component of the polycentric hinge of FIG. 3;

FIGS. 3F, 3G and 3H are respectively a side view, an outer view and a perspective inner view of the component of FIG. 3E;

FIGS. 4-7 show schematically four different possible operative configurations of the knee brace according to the present invention;

DETAILED DESCRIPTION OF EMBODIMENTS OF THE INVENTION

Figure 1B:
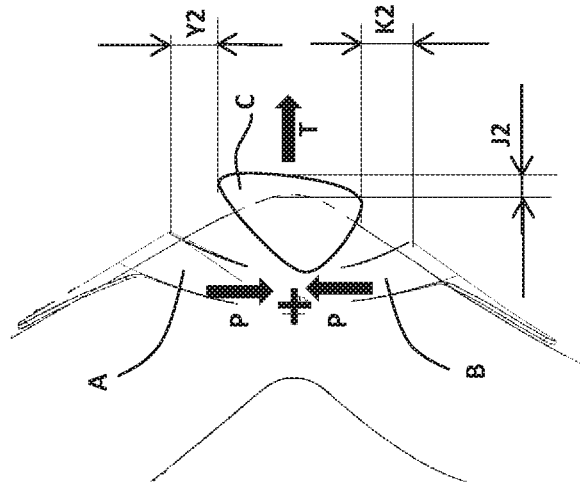
Figure 1A:
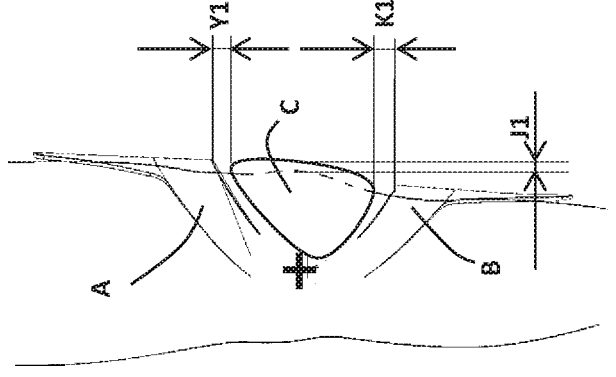

With reference to the enclosed figures, a polycentric hinge according to the invention is indicated as a whole by the reference 10.

The polycentric hinge 10, which for sake of clarity hereinafter will be named hinge, is designed for being used in a knee brace 20 such as that shown in FIGS. 20-22.

In the description of the hinge 10 and the knee brace 20 and their individual components which will be provided below, "upper" will be used to indicate a component or a part thereof, which in use is relatively distant from the ground, while "lower" will be used to indicate a component or a part thereof, which in use is relatively closer to the ground.

Preferably, the hinge 10 is designed for articulating to each other an upper frame 22 and a lower frame 24 of a knee brace 20 suitable for being used by motorcyclists, particularly by motocross riders. As it is well known in the art and schematically shown in FIGS. 4-7, the upper frame 22 is designed to be fastened to the upper part 4 of the user's leg 2 and the lower frame 24 is designed to be fastened to the lower part 6 of the user's leg 2.

At the same time, the knee brace 20 can also be used in other fields where an effective protection of the user's legs must be obtained. For example, the knee brace 20 can advantageously be used by cyclists or skiers.

Moreover, the hinge 10 can also be used in orthopedic knee braces 20 designed to control and limit the knee joint movements.

Figure 2:
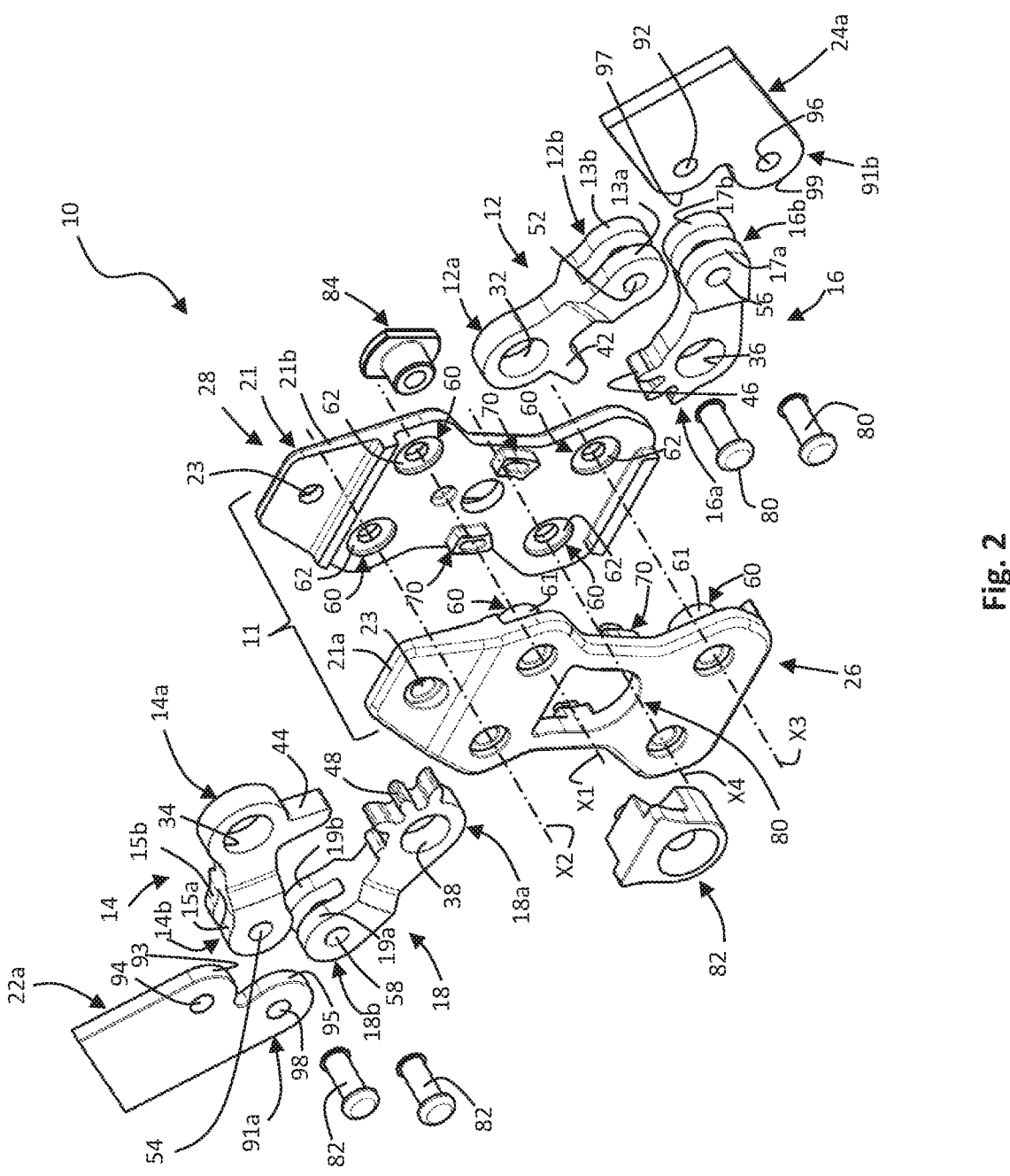
FIG. 2 shows a schematic exploded view of a first embodiment of the polycentric hinge according to the present invention.

With reference to FIG. 2, the hinge 10 comprises a first couple of hinge arms, formed by a first hinge arm 12 and a second hinge arm 14, and a second couple of hinge arms, formed by a third hinge arm 16 and a fourth hinge arm 18.

Moreover, the hinge 10 comprises a hinge body 11 configured for hinging together the first couple of hinge arms 12, 14 and the second couple of hinge arms 16, 18.

As shown in the enclosed figures, each hinge arm 12, 14 of the first couple and each hinge arm 16, 18 of the second couple has a first end 12a, 14a, 16a, 18a pivotally enclosed inside the hinge body 11 (see for example FIGS. 2, 10, 13, 16 and 19).

In particular, the hinge body 11 is provided with pivoting means 60 adapted to engage the first ends 12a, 14a, 16a, 18a of the hinge arms 12, 14, 16, 18 to define four different and spaced apart rotation axes X1, X2, X3, X4 extending transversally with respect to a longitudinal axis P of the hinge body 11.

The pivoting means 60 engaging the first end 12a of the first hinge arm 12 and the first end 14a of the second hinge arm 14 define a first rotation axis X1 of the first arm 12 and a second rotation axis X2 of the second arm 14, respectively.

Similarly, the pivoting means 60 engaging the first end 16a of the third hinge arm 16 and the first end 18a of the fourth hinge arm 18 define a third rotation axis X3 of the third arm 16 and a fourth rotation axis X4 of the fourth arm 18, respectively. Moreover, each hinge arm 12, 14 of the first couple and each hinge arm 16, 18 of the second couple has a second end 12b, 14b, 16b, 18b pivotally fixed to a mounting frame 22a, 24a.

Preferably, the second end 12b of the first hinge arm 12 and the second end 16b of the third hinge arm 16 are fixed to a first mounting frame 24*a*, while the second end 14*b* of the second hinge arm 14 and the second end 18*b* of the fourth hinge arm 18 are fixed to a second mounting frame 22*a*.

As it will be disclosed in detail in the following, first and second mounting frames 22*a*, 24*a* can be integral with the upper and lower frames 22, 24 of the knee brace 20, respectively. Alternatively, the first and second mounting frame 22*a*, 24*a* can be directly or indirectly fixed to the upper and lower frames 22, 24 of the knee brace 20.

As shown for example in FIGS. 10, 13, 16, 19, the first ends 16*a*, 18*a* of each hinge arm 16, 18 of the second couple are designed to be connected to each other, so that a rotation of the mounting frame 22*a*, 24*a* causes a rotation of both hinge arms 16, 18 around their respective rotation axes X3, X4.

In detail, a rotation of one of the mounting frames 22*a*, 24 will result in a first rotation of the third (or fourth) arm around its rotation axis X3 (or X4) and in a second rotation of the fourth (or third) arm equal and opposite to the first rotation around its rotation axis X4 (or X3) (see FIGS. 8, 11, 14, 17).

As it will appear clearly from the following description, the mutual arrangement of the first couple of hinge arms 12, 14 and second couple of hinge arms 16, 18 with respect to the hinge body 11 and the mounting frames 22*a*, 24*a* allows to obtain a hinge 10 in which four different and spaced apart rotation axes X1, X2, X3, X4 of the hinge arms 12, 14, 16, 18 are defined. In this way, the hinge 10 is able to better adapt to the rotation of the knee joint during the movements of the user's leg.

At the same time, the provision of a second couple of hinge arms 16, 18 having their first ends 16*a*, 18*a* connected to each other permit to synchronize the movement of the hinge arms 16, 18 of the second couple about their rotation axes X3, X4 and to have a simultaneous rotation of the hinge arms 12, 14 of the first couple about their rotation axes X1, X2.

Finally, the provision of a hinge body 11 designed to enclose and to hinge the first ends 12*a*, 14*a*, 16*a*, 18*a* of the hinge arms 12, 14, 16, 18 permits to obtain a hinge 10 having the needed rigidity to protect the knee joint against knee twisting.

In the following description, the structure of each element forming the hinge 10 will be described in detail, starting from the hinge body 11.

Figures 8, 9, 10, 11, 12, 13:
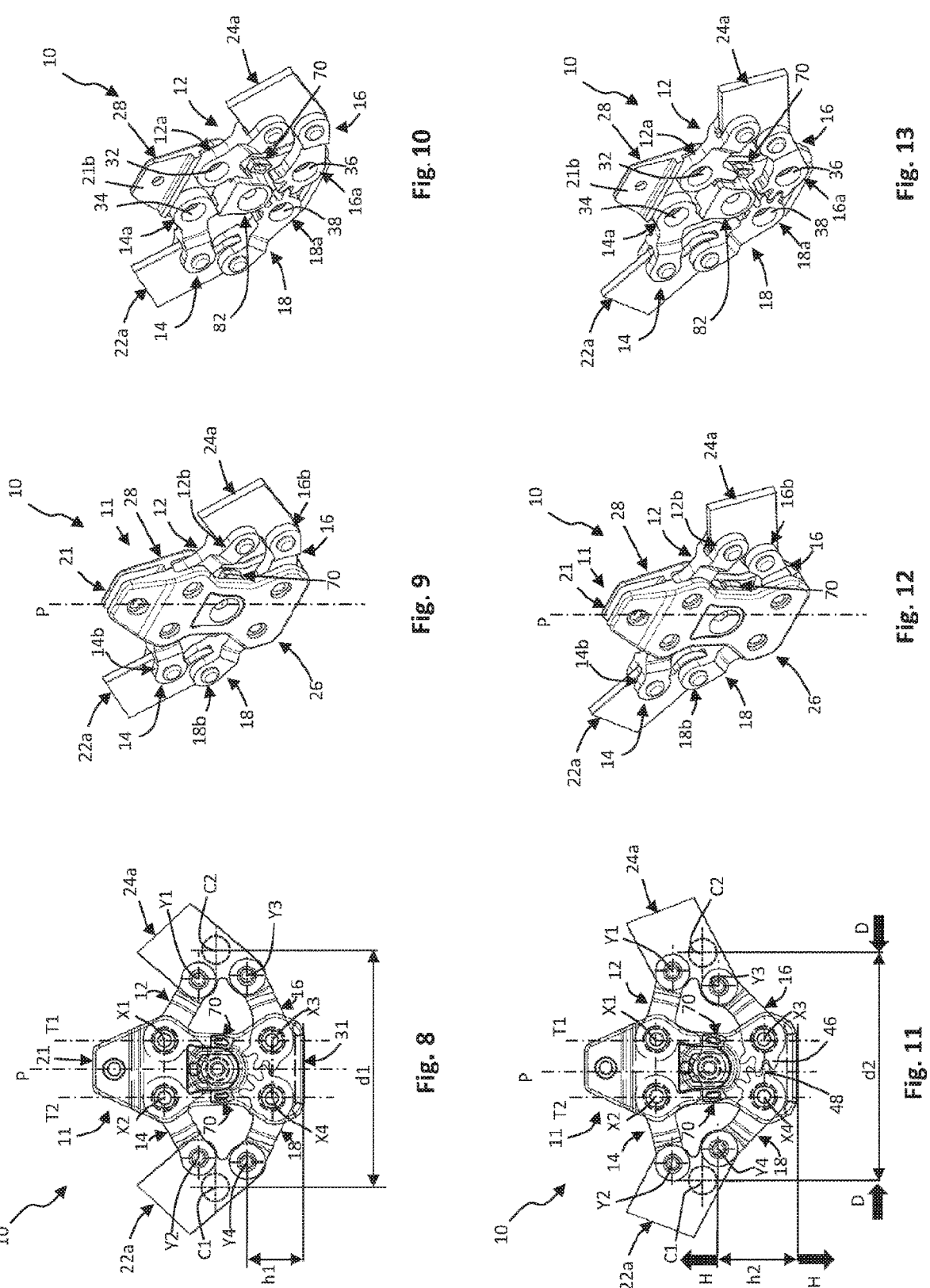
FIG. 8 shows a partially transparent front view of the polycentric hinge according to the invention; the polycentric hinge being in a first operative configuration corresponding to the knee brace configuration of FIG. 4.
FIG. 9 shows a perspective view of the polycentric hinge of FIG. 8.
FIG. 10 shows a view similar to FIG. 9, wherein one of the cover plates of the hinge has been removed for clarity reasons.
FIG. 11 shows a view of the polycentric hinge of FIG. 8 in a second operative configuration corresponding to the knee brace configuration of FIG. 5.
FIGS. 12 and 13 show views similar to FIGS. 9 and 10 but relating to the operative configuration of FIG. 11.

Preferably, the hinge body 11 is symmetrical about the longitudinal axis P of the hinge body 11 (see for example FIGS. 8-9; 11-12; 14-15; 17-18; 20-22). Advantageously, the hinge body 11 comprises a first cover plate 26 and a second cover plate 28 designed to be coupled to each other.

The second cover plate 28 is designed to be positioned facing the knee joint of the user. Preferably, a foam padding layer, not visible in the enclosed figures, can be applied to the second cover plate 28 to provide comfort and further support to the knee joint.

First cover plate 26 and second cover plate 28 are preferably coupled in a spaced apart configuration by means of spacing means 70 (see for example FIGS. 2, 8, 11) so that the first ends 12*a*, 14*a*, 16*a*, 18*a* of the hinge arms 12, 14, 16, 18 are encased between first and second cover plates 26, 28.

Thanks to the spaced apart arrangement of the cover plates 26, 28 the rotation movements of the hinge arms 12, 14, 16, 18 are not hindered.

Advantageously, identifying as "inner surface" of the first and second cover plates 26, 28, the surface thereof not visible when the hinge 10 is assembled, the spacing means 70 preferably comprise at least four spacers, two spacers being provided on the inner surface of the first cover plate 26 and two spacers being provided on the inner surface of the second cover plate 28 (see FIGS. 3A-3H).

The spacers provided on the first cover plate 26 and/or on the second cover plate 28 can comprise a fastening pin which protrudes from a supporting base and is designed to be inserted inside a corresponding seat of a juxtaposed supporting base provided on the second cover plate 28 and/or on the first cover plate 26. In this way, the correct centering between first and second cover plates 26, 28 is assured.

The spacing means 70 can advantageously be of the snap fit type. Alternatively, the spacing means 70 can be combined with rivets or screws designed to hold together the spacers.

Advantageously, the pivoting means 60 provided in the hinge body 11 can comprise a plurality of protruding pins 61 and a plurality of corresponding recesses 62.

Preferably, four cylindrical shaped recesses 62 are provided on the second cover plate 28; said recesses 62 being adapted to house at least partially corresponding cylindrical shaped pins 61 provided on the first cover plate 26, when the cover plates 26, 28 are fastened to each other (see FIGS. 3A-3E).

When the hinge 10 is assembled, the pins 61 engage the first ends 12*a*, 14*a*, 16*a*, 18*a* of the first couple and second couple of hinge arms 12, 14, 16, 18 before being received in the corresponding recesses 62.

As before mentioned, the pivoting means 60 are provided in the hinge body 11 to define the rotation axes X1, X2, X3, X4. In particular, the pins 61 designed to engage the first end 16*a* of the third arm 16 and the first end 18*a* of the fourth arm 18 are spaced apart to each other, so as to allow the first end 16*a* and the first end 18*a* to be connected to each other.

Figure 3:
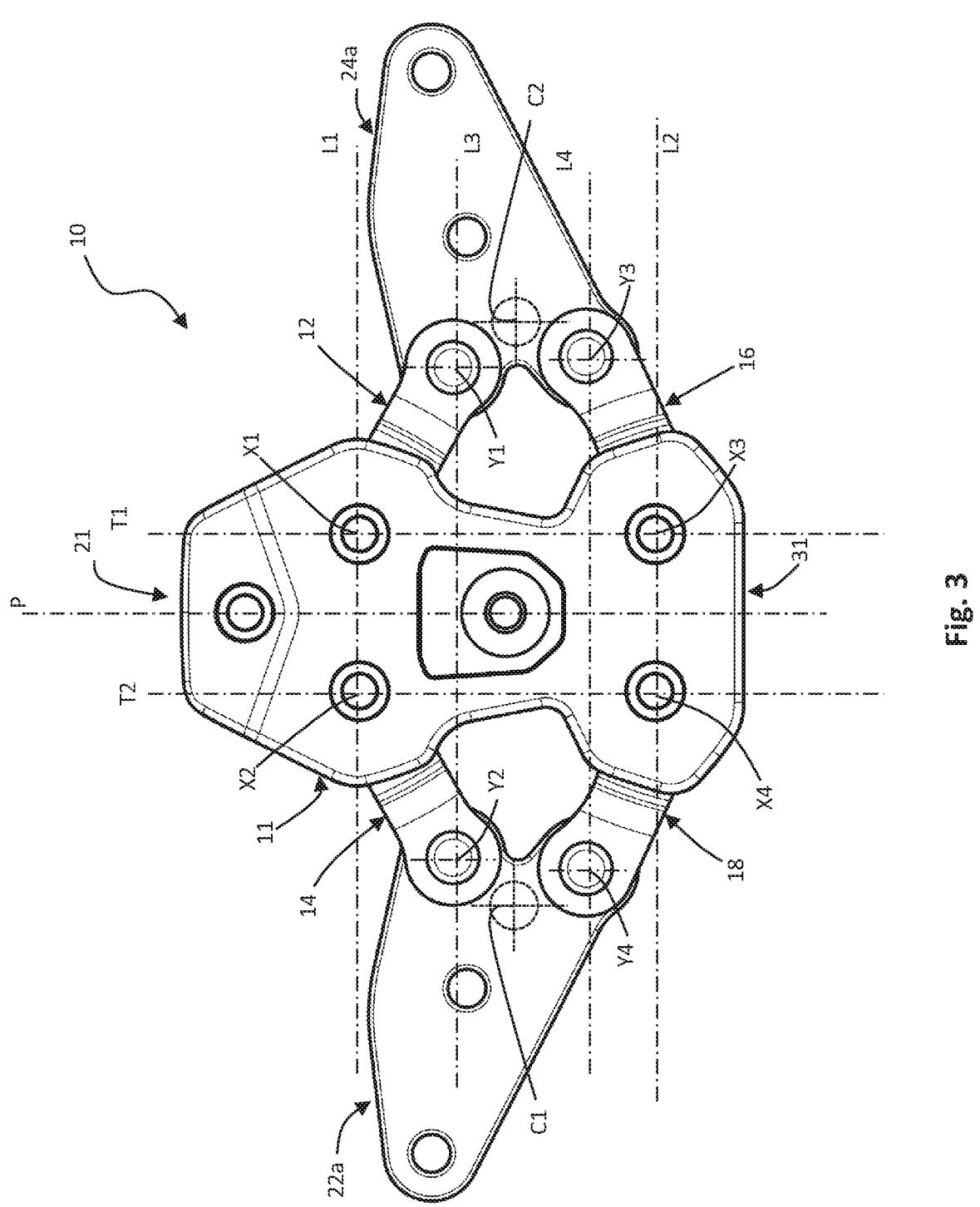
FIG. 3 shows a front view of the polycentric hinge of FIG. 2 in an assembled configuration.

Moreover, as shown in the enclosed figures, the pins 61 and the recesses 62 are provided in the hinge body 11 so that the first rotation axis X1 is symmetrical to the second rotation axis X2 with respect to the longitudinal axis P of the hinge body 11; the first rotation axis X1 and the second rotation axis X2 extending parallel to each other and lying on the same plane L1 (see FIG. 3).

Similarly, the pins 61 and the recesses 62 are provided in the hinge body 11 so that the third rotation axis X3 is symmetrical to the fourth rotation axis X4 with respect to the longitudinal axis P of the hinge body 11; the third rotation axis X3 and the fourth rotation axis X4 extending parallel to each other and lying on the same plane L2 (see FIG. 3).

Advantageously, as shown in the enclosed figures, the first rotation axis X1 is also parallel and aligned with the third rotation axis X3 along a plane T1 and the second rotation axis X2 is also parallel and aligned with the fourth rotation axis X4 along a plane T2. The planes T1 and T2 are parallel to the longitudinal axis P of the hinge body 11.

Figures 20, 21, 22:
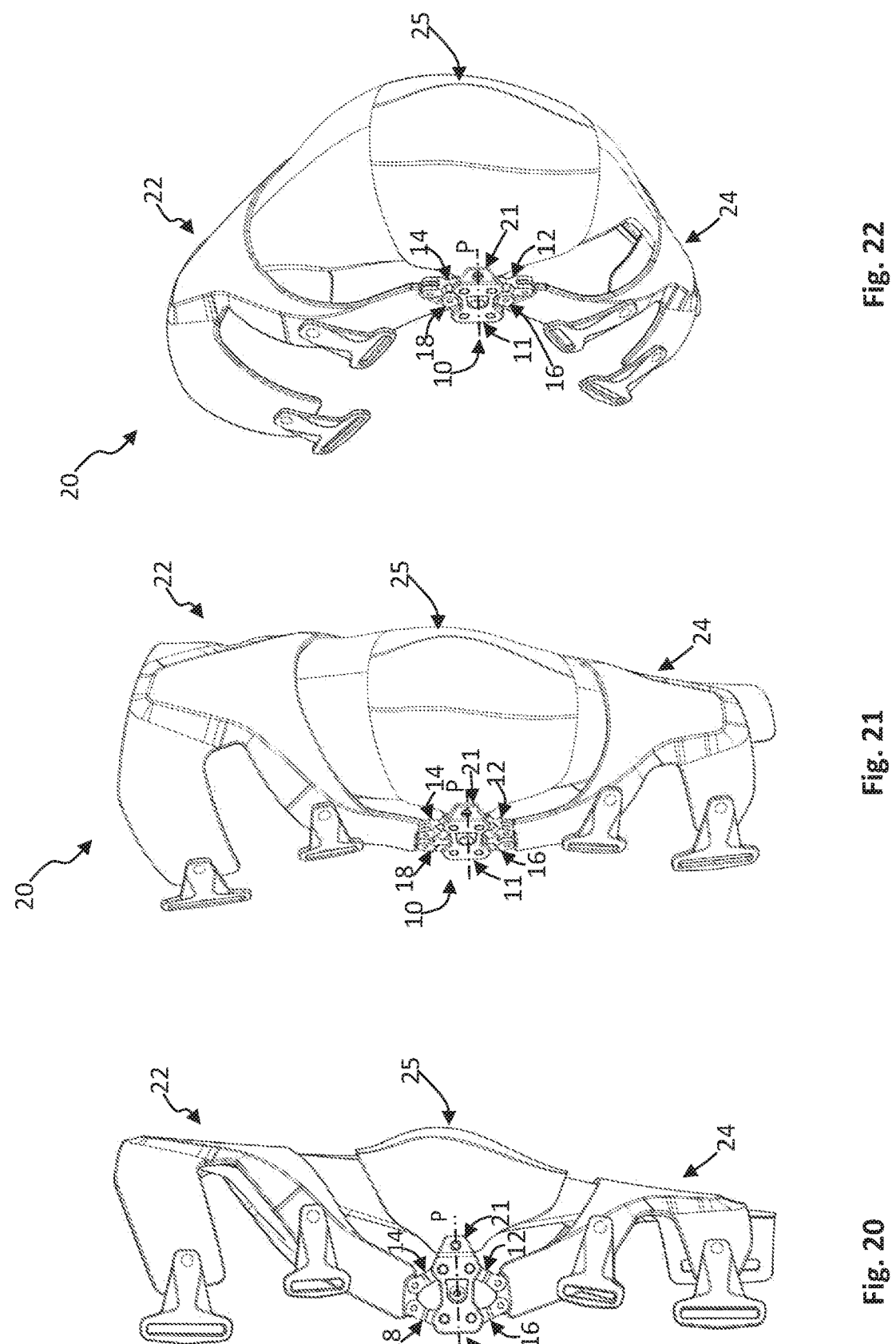
FIG. 20 shows a side view of the knee brace of the present invention in a first operative configuration.
FIG. 21 shows a perspective view of the knee brace of FIG. 20.
FIG. 22 shows a view similar to FIG. 21, but in a different operative configuration.

The hinge body 11 can also be provided with a fastening appendix 21 configured to be fastened to a knee protecting cup 25 of the knee brace 20 (as shown in FIGS. 20-22).

Preferably, the fastening appendix 21 consists in a bearing fork formed by two spaced apart lugs 21*a*, 21*b*, each provided with a fastening through hole 23. Preferably, the fastening hole 23 is arranged along the longitudinal axis P of the hinge body 11.

If the hinge body 11 is formed by a first cover plate 26 and a second cover plate 28, a first lug 21*a* will be provided on the first cover plate 26 and a second lug 21*b* will be provided on the second cover plate 28.

The fastening appendix 21 is designed to accept a side appendix of the knee cup 25, which can be fixed therein by means of a fastening pin or rivet engaging the fastening hole 23.

Such a fastening pin or rivet can also be used to close together the first and second cover plates 26, 28 and the whole hinge mechanism.

The hinge body 11 can also be provided with a central slot 80 designed to house an extension stop 82, having the function to limit the rotation of hinge arms 12, 14, 16, 18 relative to one another to prevent unnatural and/or dangerous movements, for example a hyperextension, of the knee.

In particular, the extension stop 82 is designed to directly interact with the first end 12a of the first arm 12 and the first end 14a of the second arm 14.

The extension stop 82 can be fixed inside the central slot 80 of the hinge body 11 by means of a fastening pin 84, for example a T-nut.

Advantageously, the extension stop 82 is arranged in the space delimited by the first and second cover plates 26, 28.

The hinge 10 can be provided with a plurality of extension stops 82 designed to stop the rotation of the first arm 12 and second arm 14 around their corresponding rotation axes X1, X2 at predefined degrees of rotation, so as to prevent that the rotation of the lower frame 24 of the knee brace 20 with respect to the upper frame 22 of the knee brace 20 exceeds a predefined angle.

The user will use the extension stop 82 more adapted to his needs and/or to the conditions of use of the knee brace.

The hinge arms 12, 14 of the first couple have advantageously the same shape and size and they are symmetrically hinged to the hinge body 11 with respect to the longitudinal axis P of the hinge body (see FIGS. 8, 11, 14, 17).

Preferably, the first end 12a, 14a of each hinge arm 12, 14 has a rounded shape and it is provided with an appendix 42, 44 designed to get in contact with the extension stop 82 inserted inside the hinge body 11 to stop the mutual rotation of the hinge arms.

The first end 12a, 14a of each hinge arm 12, 14 can delimit first connecting holes 32, 34 adapted to be engaged by the corresponding pivoting means 60 provided in the hinge body 11.

The second end 12b, 14b of each hinge arm 12, 14 in turn can be in the form of a bearing fork, having two lugs 13a, 13b, 15a, 15b, each provided with a fastening through hole 52, 54.

The fastening holes 52 arranged in the second end 12b of the first arm 12 and the fastening holes 54 arranged in the second end 14b of the second arm 14 define a first additional rotation axis Y1 and a second additional rotation axis Y2, respectively.

Moreover, once the hinge 10 is assembled, the additional rotation axes Y1, Y2 defined by the second ends 12b, 14b of the hinge arms 12, 14 are parallel and lie on the same plane L3 (see FIG. 3). The additional rotation axes Y1 and Y2 are also symmetrical with respect to the longitudinal axis P of the hinge body 11.

Similarly to the hinge arms 12, 14 of the first couple, the hinge arms 16, 18 of the second couple have advantageously same shape and size and they are symmetrically hinged to the hinge body 11 with respect to the longitudinal axis P of the hinge body (see FIGS. 8, 11, 14, 17).

As shown in the enclosed figures, the second couple of hinge arms is fastened to the hinge body in a position opposite to the fastening appendix 21. Preferably the third arm 16 is fastened to the hinge body so as to be adjacent to the first arm 12 and the fourth arm 18 is fastened to the hinge body so as to be adjacent to the second arm 14 (see FIG. 3).

Advantageously, the hinge arms 16, 18 have a curved inner side, where as inner side is intended to be the side of the hinge arms 16, 18 which faces towards the adjacent hinge arm 12, 14 of the first couple once the hinge 10 is assembled.

Preferably, the first end 16a, 18a of each hinge arms 16, 18 of the second couple has a rounded shape and they can delimit first connecting holes 36, 38 adapted to be engaged by the corresponding pivoting means 60 provided in the hinge body 11.

Advantageously, the first ends 16a, 18a of each hinge arm 16, 18 of the second couple can be provided along the respective perimeter edges with gear teeth 46, 48 designed to mesh during rotation of the corresponding hinge arms 16, 18 following a rotation movement of the mounting frames 22a, 24a.

Preferably, the second end 16b, 18b of each hinge arm 16, 18 in turn is in the form of a bearing fork, having two lugs 17a, 17b, 19a, 19b, each provided with a fastening through hole 56, 58.

The fastening holes 56 arranged in the second end 16b of the third arm 16 and the fastening holes 58 arranged in the second end 18b of the fourth arm 18 define a third additional rotation axis Y3 and a fourth additional rotation axis Y4, respectively.

Once the hinge is assembled, the additional rotation axes Y3, Y4 defined by the second ends 16b, 18b of the hinge arms 16, 18 are parallel and lie on the same plane L4 (see FIG. 3). The additional rotation axes Y3 and Y4 are also symmetrical with respect to the longitudinal axis P of the hinge body 11.

As shown in the enclosed figures, the mounting frames 22a and 24a can be fastened to the hinge arms 12, 14, 16, 18 of the hinge 10 at the second ends 12b, 14b, 16b, 18b.

Specifically, the lower mounting frame 24a can be fastened at the second end 12b of the first arm 12 and at the second end 16b of the third arm 16, while the upper mounting frame 22a can be fastened at the second end 14b of the second arm 14 and at the second end 18b of the fourth arm 18.

Preferably, a lower end 91a of the upper mounting frame 22a is provided with at least two second connecting holes 94, 98.

Said lower end 91a is designed to be positioned inside the bearing forks provided at the second ends 14b, 18b of the second and fourth arms 14, 18 so that the second connecting holes 94, 98 can be aligned with the fastening through holes 54, 58. The lower end 91a can be blocked therein, by means of blocking means 82, for example rivets, engaging the second connecting holes 94, 98 and the fastening through holes 54, 58.

Similarly, an upper end 91b of the lower mounting frame 24a can be provided with at least two second connecting holes 92, 96.

Said upper end 91b is designed to be positioned inside the bearing forks provided at the second ends 12b, 16b of the first and third arms 12, 16 so that the second connecting holes 92, 96 are aligned with the fastening through holes 52, 56. The upper end 91b can be blocked therein by means of blocking means 80, for example rivets, engaging the second connecting holes 92, 96 and the fastening through holes 52, 56.

In particular, the lower end 91a of the upper mounting frame 22a and the upper end 91b of the lower mounting frame 24a can be each provided with two staggered lobes

93, 95, 97, 99, each one designed to be inserted inside a corresponding bearing fork of the hinge arms 12, 14, 16, 18.

The second connecting holes 94, 98, 92, 96 are preferably arranged on the staggered lobes 93, 95, 97, 99 of the ends 91a, 91b.

The second connecting holes 94, 98 provided in the lower end 91a when the hinge is assembled are symmetrical with respect to the second connecting holes 92, 96 provided in the upper end 91b.

Specifically, a first lobe 93 of the lower end 91a, provided with the second connecting hole 94, is fastened to the bearing fork 14b of the second arm 14 and a second lobe 95 of the lower end 91a, provided with the second connecting hole 98, is fastened to the bearing fork 18b of the fourth arm 18.

Similarly, a first lobe 97 of the upper end 91b, provided with the second connecting hole 92, is fastened to the bearing fork 12b of the first arm 12 and a second lobe 99 of the upper end 91b, provided with the second connecting hole 96, is fastened to the bearing fork 16b of the third arm 16.

As before mentioned, the fastening holes 52, 54, 56, 58, which are designed to be coupled with the second connecting holes 92, 94, 96, 98, define the additional rotation axes Y1, Y2, Y3, Y4.

Due to the staggered position of the second connecting hole 96 of the lobe 99 with respect to the second connecting hole 92 of the lobe 97, during the movement of the first and third hinge arms 12, 16, the third additional rotation axis Y3 will be movable around the first additional rotation axis Y1.

Similarly, due to the staggered position of the second connecting hole 98 of the lobe 95 with respect to the second connecting hole 94 of the lobe 93, during the movement of the second and fourth hinge arms 14, 18, the fourth additional rotation axis Y4 will be movable around the second additional rotation axis Y2.

The mutual movement between first and third additional rotation axis Y1, Y3 and the corresponding mutual movement of the second and fourth additional rotation axis Y2, Y4 permit the facing ends 91a, 91b of the upper and lower frames 22, 24 of the knee brace 20 to get closer during the flexion movement of the knee brace, without resulting in a movement of the hinge body 11 towards an outward direction, namely towards the patella of the user.

Consequently, the protecting cup 25, which is fastened to the hinge body 11 of the hinge 10 at the appendix 21, during the various movements of the knee brace 20 will be able to stay closer to the patella of the user and to the upper and lower frames 22, 24 of the knee brace 20 to guarantee an improved protection to the user.

How the hinge 10 works during the movements of the knee brace 20 to which it is affixed will be explained in detail by making reference to FIGS. 3; 4-7; 8-10; 11-13; 14-16 and 17-19.

In the following it will be assumed that the upper mounting frame 22a of the hinge 10 is integral with the upper frame 22 of the knee brace 20 and that the lower mounting frame 22b of the hinge 10 is integral with the lower frame 24 of the knee brace 20.

However, the same comments are still valid in case of a direct or indirect connection between mounting frames 22a, 22b and corresponding frames 22, 24 of the knee brace 20.

In view of the above description, a rotation of the lower frame 24 of the knee brace 20 with respect to the upper frame 22 of the knee brace 20 results in a corresponding rotation of the lower mounting frame 22b of the hinge 10 with respect to the upper mounting frame 22a of the hinge 10.

Figure 4:
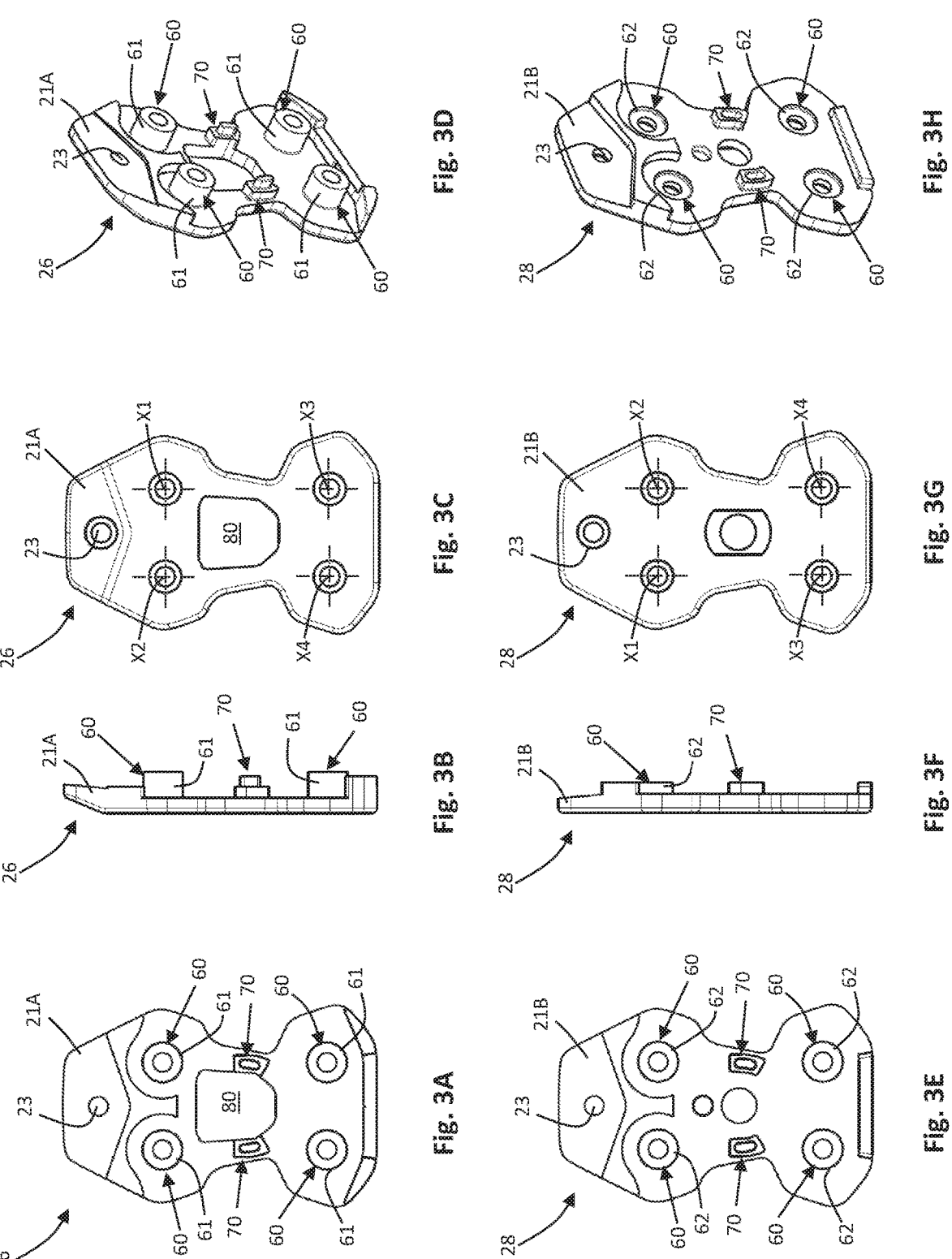

By way of example, the movements of the hinge 10 in three different angulated configurations of the knee brace (see schematic FIGS. 5-7) will be illustrated starting from a straight configuration of the knee brace 20 (see FIG. 4). To better show the movements of the user's leg, the knee brace 20 is sketched in a highly simplified manner in FIG. 4.

In the straight configuration the longitudinal axis U of the upper part 4 of the leg 2, namely the part of the leg comprised between the patella and the waist of the user, is substantially aligned with the longitudinal axis B of the lower part 6 of the leg 2, namely the part of leg comprised between the patella and the foot of the user.

In a first angulated configuration shown in FIG. 5, the longitudinal axis B of the lower part 6 of the leg 2 forms with the longitudinal axis U of the upper part 4 of the leg 2 an angle $\alpha 1$ of about 30°, while in a second angulated configuration (see FIG. 6) and in a third angulated configuration (see FIG. 7), the longitudinal axis B of the lower part 6 of the leg 2 forms with the longitudinal axis U of the upper part 4 of the leg 2 an angle $\alpha 2$ of about 90° and an angle $\alpha 3$ of about 120°, respectively.

In FIGS. 3, 8, 11, 14, 17 the references C1, C2 identify the rotation centers of the mounting frames 22a, 24a with respect to the hinge body 11.

Thanks to the mutual arrangement between the hinge arms 12, 14, 16, 18 and the mounting frames 22a, 24a, the position of the instant centers C1, C2 of the mounting frames 22a, 24a, following the rotation of the lower frame 24 with respect to the upper frame 22 of the knee brace 20, constantly changes to better adapt to the knee joint movements.

In detail, in the straight configuration of the knee brace 20, the hinge 10 has a configuration (see FIGS. 8-11) wherein the first arm 12 and the third arm 16 are inclined towards each other.

Similarly, the second arm 14 and the fourth arm 18 are inclined towards each other.

In such a configuration the centers of rotations C1, C2 of the mounting frames 22a, 22b, which are positioned in proximity of the corresponding lobes of the mounting frames 22a, 24a, are spaced apart of a distance, which is identified as d1 in FIG. 8. Furthermore, in the configuration of FIGS. 8-10, the additional rotation axes Y3 and Y4 are spaced apart from a terminal end 31 of the hinge body 11 of a distance, which is identified as h1 in FIG. 8. The terminal end 31 corresponds to the end of the hinge body 11 opposite to the appendix 21.

In the passage of the knee brace 20 from the straight configuration of FIG. 4 to the first angulated configuration of FIG. 5, as it is shown in FIGS. 11-13, third and fourth arms 16, 18, thanks to the meshing of their respective gear teeth 46, 48, undergo a synchronized and opposite rotation around their respective rotation axes X3, X4.

In particular, as viewed in FIG. 11, the third arm 16 has a counterclockwise rotation around the third rotational axis X3 and the fourth arm 18 has a clockwise rotation around the fourth rotational axis X4.

In view of the mutual arrangement between the second couple of hinge arm 16, 18 and the first couple of hinge arm 12, 14, the latter undergo a simultaneous rotation around their respective rotation axes X1, X2.

In particular, the first arm 12 has a counterclockwise rotation around the first rotational axis X1 and the second arm 14 has a corresponding and opposite clockwise rotation around the second rotational axis X2.

As schematically shown in FIG. 11, following the rotations of the hinge arms 12, 14, 16, 18 around their axes of rotation X1, X2, X3, X4, the distance, identified as d2, between the center of rotations C1 and C2 of the mounting frames 22a and 24a has decreased with respect to the distance d1 measured in the straight configuration of the knee brace.

This is due to the fact that each mounting frame is pivotally connected to the hinge arms in two spaced apart points which allows a relative rotation of the third and fourth additional rotation axes Y3, Y4 with respect to the first and second rotation axes Y1, Y2.

Consequently the additional rotation axes Y3 and Y4 are spaced apart from the terminal end 31 of the hinge body 11 of a distance, identified as h2, which is greater than the distance h1 measured in the straight configuration.

If, as shown by way of the example, the hinge 10 is provided with an extension stop 82 suitable for blocking the rotation of the arms when the angle between the upper part of the leg and the lower part of the leg reaches a value of 30°, the appendixes 42, 44 will make contact with the side portions of the extension stop. Consequently, being blocked the rotation of the first couple of arms 12, 14, also the rotation of the second couple of arms 16, 18 will be stopped so as not allow a further flexion of the lower part of the leg.

Figures 14, 15, 16, 17, 18, 19:
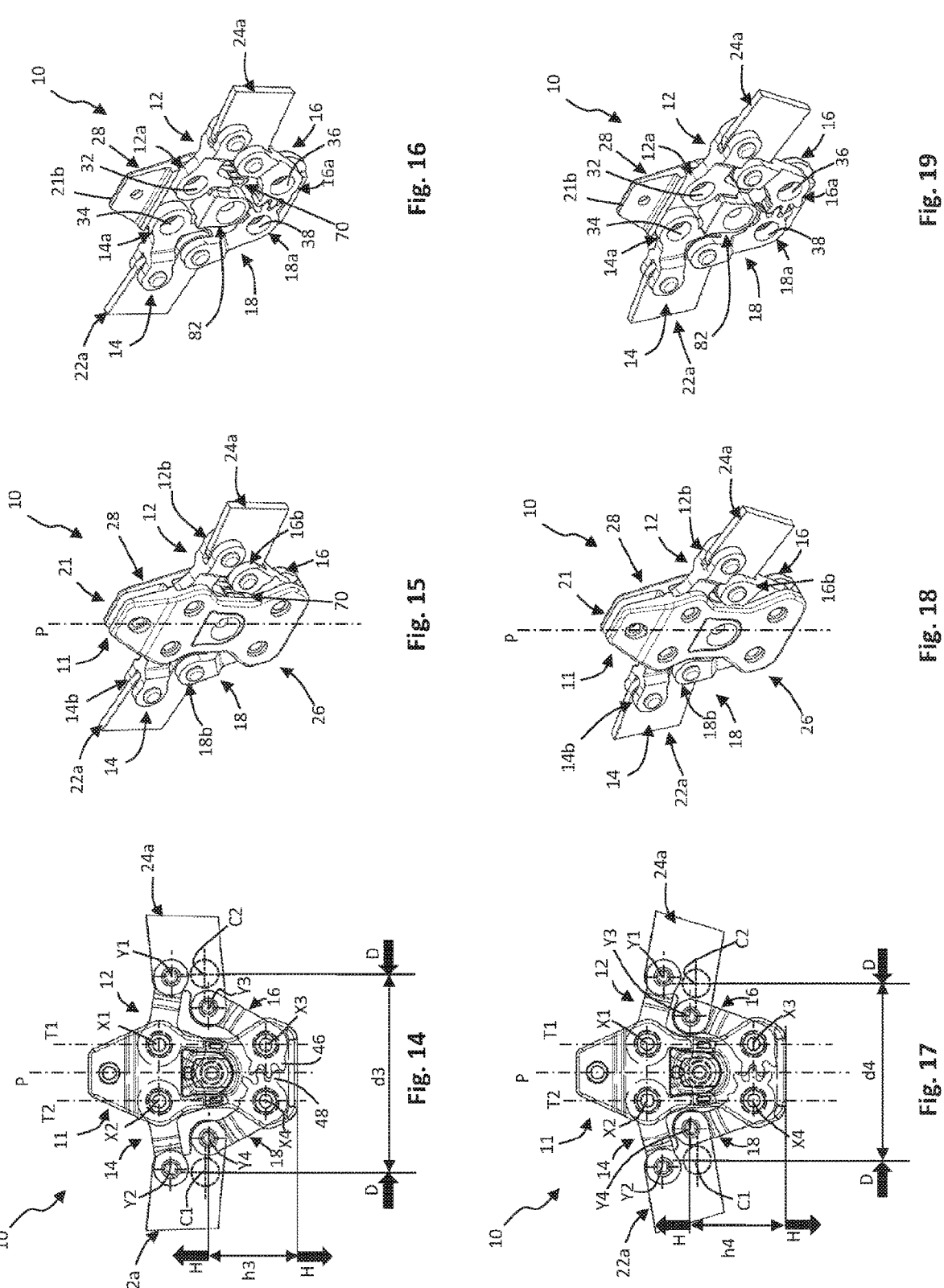
FIG. 14 shows a view of the polycentric hinge of FIG. 8 in a third operative configuration corresponding to the knee brace configuration of FIG. 6.
FIGS. 15 and 16 show views similar to FIGS. 9 and 10 but relating to the operative configuration of FIG. 14.
FIG. 17 shows a view of the polycentric hinge of FIG. 8 in a fourth operative configuration corresponding to the knee brace configuration of FIG. 7.
FIGS. 18 and 19 show views similar to FIGS. 9 and 10 but relating to the operative configuration of FIG. 17.

If the knee brace 20 moves towards the second angulated configuration of FIG. 6, third and fourth arms 16, 18 continue in their respective counterclockwise and clockwise rotations around the rotation axes X3, X4 (see FIGS. 14-16).

Following such rotations, third and fourth arms 16, 18 move closer to the side of the hinge body 11, in particular the second ends of the third and fourth arms 16, 18 get closer to the first end of the first and second hinge arms 12, 14.

First and second arms 12, 14 in turn continue in their respective counterclockwise and clockwise rotations around the rotation axes X1, X2.

As shown schematically in FIG. 14, following the rotations of the hinge arms 12, 14, 16, 18 around their axes of rotation X1, X2, X3, X4, the distance, identified as d3, between the center of rotations C1 and C2 of the mounting frames 22a and 24a has further decreased with respect to the distance d2 measured in the first angulated configuration.

Similarly, the additional rotation axes Y3 and Y4 are spaced apart from the terminal end 31 of the hinge body 11 of a distance, identified as h3, which is greater than the distance h2 measured in the first angulated configuration.

If the knee brace 20 moves towards the third angulated configuration of FIG. 7, third and fourth arms 16, 18 and first and second arms 12, 14 continue in their respective rotations around the rotation axes X1, X2, X3, X4

As shown schematically in FIG. 17, following a further rotation of the hinge arms 12, 14, 16, 18 around their axes of rotation X1, X2, X3, X4, the distance, identified as d4, between the center of rotations C1 and C2 of the mounting frames 22a and 24a has further decreased with respect to the distance d3 measured in the second angulated configuration.

Similarly, the additional rotation axes Y3 and Y4 are spaced apart from the terminal end 31 of the hinge body 11 of a distance, identified as h4, which is greater than the distance h3 measured in the second angulated configuration.

The decreasing of the distance d (indicated by the arrows D in FIGS. 11, 14, 17) between the center of rotations C1, C2 of the mounting frames 22a, 24a during the passage from the straight configuration to the various angulated configurations and the concurrent increasing of the distance h between the additional rotation axes Y3, Y4 and the terminal end 31 of the hinge body 11 (indicated by the arrows H in FIGS. 11, 14, 17) confirm that the hinge 10 permits the mounting frames 22a, 24a to follow a roto-translation movement so as to better adapt to the movements of the knee joint.

As a matter of fact, the decreasing of the distance d means that the mounting frames 22a, 24a are able to get closer to each other during the flexion movements of the knee joint without opposing it. Such a movement is schematically indicated by the arrows W in FIGS. 5-7.

Moreover, the increasing of the distance h means that following such a reduction of distance between the mounting frames 22a, 24a, the hinge body 11 does not undergo an outward movement.

On the contrary, thanks to the possibility of the third and fourth arm 16, 18 to get closer to hinge body 11, the latter undergoes a movement which is directed as schematically indicated by the arrow R in FIGS. 5-7, namely away from the protecting cup 25 which is fastened to the appendix 21.

In this way, it is assured that the protecting cup maintains its proper position in proximity of the patella of the user and that the hinge body does not move away from the sides of the knee joint, so as to guarantee support and protection to the knee joint also in a flexed condition of the knee brace.

It is thus clear how the predefined objects may be achieved with the hinge 10 and the knee brace 20 according to the invention.

As a matter of fact, the hinge 10 is able to adapt itself to the natural movements of the knee assuring an improved comfort.

At the same time, the hinge 10 is able to assure a high stability to the knee joint.

Moreover, the knee brace provided with the hinge 10 is able to offer an improved protection against impacts, since in the flexed configuration the protecting cup stays close to the patella of the user, without affecting the freedom of movement of the user.

Furthermore, thanks to the hinge 10, the user can wear the knee brace 20 under his pants without being hindered in his movements.

With regard to the embodiments of the hinge 10 and knee brace 20 described above, the person skilled in the art may, in order to satisfy specific requirements, make modifications to and/or replace elements described with equivalent elements, without thereby departing from the scope of the accompanying claims.

The invention claimed is:

1. A polycentric hinge configured to support a joint of a user, comprising:
   a first hinge arm and a second hinge arm;
   a third hinge arm and a fourth hinge arm;
   a hinge body configured for hinging together the first, second, third, and fourth hinge arms, each hinge arm having a first end pivotally enclosed inside said hinge body and a second end, the second ends of the second and fourth hinge arms are pivotally fixed to a first mounting frame, and the second ends of the first and third hinge arms are pivotally fixed to a second mounting frame;
   characterized in that the hinge body is provided with a plurality of pivoting pins adapted to engage said first ends of each of the first, second, third, and fourth hinge arms to define four different and spaced apart rotation axes extending transversally with respect to a longitudinal axis of the hinge body and in that the first ends of the third hinge arm and the fourth hinge arm are connected to each other, so that a rotation of the first mounting frame with respect to the second mounting frame causes a rotation of the third and fourth hinge arms around their respective rotation axes.

2. The polycentric hinge according to claim 1, characterized in that the second end of each of the first and second hinge arms are formed as a bearing fork, said bearing fork having two lugs each provided with a fastening through hole.

3. The polycentric hinge according to claim 2, characterized in that the fastening through holes arranged in the second end of the first hinge arm define a fifth rotation axis and the fastening through holes arranged in the second end of the second hinge arm define a sixth rotation axis, the fifth rotation axis and the sixth rotation axis being symmetrical with respect to the longitudinal axis of the hinge body.

4. The polycentric hinge according to claim 3, characterized in that the second end of each of the third and fourth hinge arms are formed as a bearing fork, said bearing fork, having two lugs each provided with a fastening through hole.

5. The polycentric hinge according to claim 4, characterized in that the fastening through holes arranged in the second end of the third hinge arm define a seventh rotation axis and the fastening through holes arranged in the second end of the fourth hinge arm define an eighth rotation axis, the seventh rotation axis and the eighth rotation axis being symmetrical with respect to the longitudinal axis of the hinge body.

6. The polycentric hinge according to claim 5, characterized in that the first mounting frame is an upper mounting frame and the second mounting frame is a lower mounting frame, the second end of the first hinge arm and the second end of the third hinge arm are fastened to the lower mounting frame and in that the second end of the second hinge arm and the second end of the fourth hinge arm are fastened to the upper mounting frame.

7. The polycentric hinge according to claim 6, characterized in that a lower end of the upper mounting frame is provided with at least two connecting holes and in that an upper end of the lower mounting frame is provided with at least two connecting holes, said lower end of the upper mounting frame being configured to be positioned inside the bearing forks provided at the second ends of the second and fourth hinge arms respectively, and said upper end of the lower mounting frame being configured to be positioned inside the bearing forks provided at the second ends of the first and third hinge arms respectively.

8. The polycentric hinge according to claim 7, characterized in that said at least two connecting holes of the lower end of the upper mounting frame are configured to be aligned with the fastening through holes of the bearing forks provided at the second ends of the second and fourth hinge arms respectively and in that said at least two connecting holes of the upper end of the lower mounting frame are configured to be aligned with the fastening through holes of the bearing forks provided at the second ends of the first and third hinge arms respectively.

9. The polycentric hinge according to claim 8, characterized in that the connecting holes provided in the lower end of the upper mounting frame are symmetrical with respect to the connecting holes provided in the upper end of the lower mounting frame.

10. The polycentric hinge according to claim 1, characterized in that said first hinge arm and said second hinge arm have a same shape and size and are symmetrically hinged to the hinge body with respect to the longitudinal axis of the hinge body, a first pivoting pin of the plurality of pivoting pins engaging the first end of the first hinge arm defining a first rotation axis of the four different and spaced apart rotation axes and a second pivoting pin of the plurality of pivoting pins engaging the first end of the second hinge arm defining a second rotation axis of the four different and spaced apart rotation axes.

11. The polycentric hinge according to claim 10, characterized in that said third hinge arm and said fourth hinge arm have a same shape and size and are symmetrically hinged to the hinge body with respect to the longitudinal axis of the hinge body, a third pivoting pin of the plurality of pivoting pins engaging the first end of the third hinge arm defining a third rotation axis of the four different and spaced apart rotation axes and a fourth pivoting pin of the plurality of pivoting pins engaging the first end of the fourth hinge arm defining a fourth rotation axis of the four different and spaced apart rotation axes.

12. The polycentric hinge according to claim 11, characterized in that the plurality of pivoting pins are provided in the hinge body so that the first rotation axis is symmetrical to the second rotation axis with respect to the longitudinal axis of the hinge body and the third rotation axis is symmetrical to the fourth rotation axis with respect to the longitudinal axis of the hinge body.

13. The polycentric hinge according to claim 12, characterized in that the first rotation axis is parallel and aligned with the third rotation axis along a first plane and the second rotation axis is parallel and aligned with the fourth rotation axis along a second planes said first and second planes being parallel to the longitudinal axis of the hinge body.

14. The polycentric hinge according to claim 1, characterized in that said hinge body comprises a first cover plate and a second cover plate coupled to each other.

15. The polycentric hinge according to claim 14, characterized in that first cover plate and second cover plate are coupled in a spaced apart configuration by a plurality of spacers so that the first ends of each of the hinge arms are encased between first cover plate and second cover plate.

16. The polycentric hinge according to claim 1, characterized in that the hinge body is symmetrical about the longitudinal axis.

17. The polycentric hinge according to claim 1, characterized in that the hinge body comprises a plurality of corresponding recesses for receiving the plurality of pivoting pins.

18. The polycentric hinge according to claim 1, characterized in that the first end of the first and second hinge arms each have a rounded shape and are provided with a protrusion configured to contact an extension stop inserted inside the hinge body to stop a rotation of the first and second hinge arms.

19. The polycentric hinge according to claim 1, characterized in that the first ends of each of the third and fourth hinge arms are provided with gear teeth designed to mesh together during the rotation of the third and fourth hinge arms following a rotation of the first mounting frame and the second mounting frame respectively.

20. The polycentric hinge according to claim 1, characterized in that the hinge body is provided with a fastening portion configured to be fastened to a knee protecting cup of a knee brace.

21. A knee brace comprising an upper frame, a lower frame and a knee protecting cup, the knee brace being characterized in that the upper frame and the lower frame are articulated to each other by means of at least one polycentric hinge according to claim 1.

* * * * *